(12) United States Patent
Brazdil et al.

(10) Patent No.: US 9,550,729 B2
(45) Date of Patent: Jan. 24, 2017

(54) MIXED METAL OXIDE CATALYSTS

(71) Applicants: James F. Brazdil, Glen Ellyn, IL (US); Mark A. Toft, Somonauk, IL (US); Stephen T. McKenna, Naperville, IL (US)

(72) Inventors: James F. Brazdil, Glen Ellyn, IL (US); Mark A. Toft, Somonauk, IL (US); Stephen T. McKenna, Naperville, IL (US)

(73) Assignee: INEOS EUROPE AG, Rolle (CH)

( * ) Notice: Subject to any disclaimer, the term of this patent is extended or adjusted under 35 U.S.C. 154(b) by 0 days.

(21) Appl. No.: 15/225,956

(22) Filed: Aug. 2, 2016

(65) Prior Publication Data

US 2016/0340296 A1 Nov. 24, 2016

Related U.S. Application Data

(62) Division of application No. 13/200,219, filed on Sep. 21, 2011, now Pat. No. 9,433,929.

(51) Int. Cl.
| | |
|---|---|
| *C07C 253/26* | (2006.01) |
| *B01J 23/00* | (2006.01) |
| *B01J 23/887* | (2006.01) |
| *G01N 23/20* | (2006.01) |

(52) U.S. Cl.
CPC ............ *C07C 253/26* (2013.01); *B01J 23/002* (2013.01); *B01J 23/8878* (2013.01); *G01N 23/20* (2013.01); *B01J 2523/00* (2013.01)

(58) Field of Classification Search
None
See application file for complete search history.

(56) References Cited

U.S. PATENT DOCUMENTS

| | | | | |
|---|---|---|---|---|
| 3,959,341 A | * | 5/1976 | Dunn | ............... C07C 253/26 422/168 |
| 3,961,896 A | * | 6/1976 | Dunn | ............. G01N 33/0013 422/90 |
| 5,378,668 A | * | 1/1995 | Beuke | .................. B01J 23/92 502/20 |
| 7,592,483 B2 | * | 9/2009 | Dieterle | ............... C07C 45/35 562/512.2 |
| 2006/0004227 A1 | * | 1/2006 | Dieterle | ............... C07C 45/35 562/526 |

FOREIGN PATENT DOCUMENTS

JP EP1634645 * 4/2004

* cited by examiner

*Primary Examiner* — Melvin C Mayes
*Assistant Examiner* — Colette Nguyen
(74) *Attorney, Agent, or Firm* — James P. Krueger

(57) ABSTRACT

Catalytic compositions are provided that are effective for providing increased acrylonitrile product without a significant decrease in hydrogen cyanide and/or acetonitrile production and provide an overall increase in production of acrylonitrile, hydrogen cyanide and acetonitrile. The catalytic compositions include a complex of metal oxides and include at least about 15% m-phase plus t-phase by weight and have a weight ratio of m-phase to m-phase plus t-phase of 0.45 or greater.

8 Claims, 1 Drawing Sheet

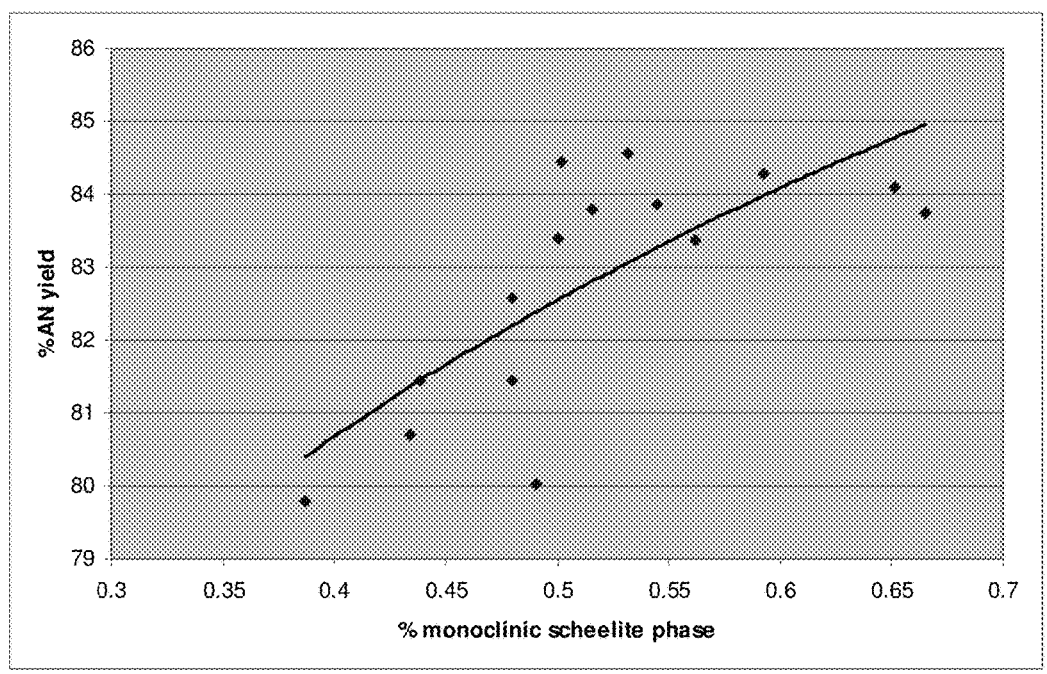

MIXED METAL OXIDE CATALYSTS

Catalytic compositions for ammoxidation of an unsaturated hydrocarbon to a corresponding unsaturated nitrile are provided. More specifically, catalytic compositions are provided that include a complex of metal oxides effective for conversion of propylene to acrylonitrile, hydrogen cyanide and acetonitrile.

BACKGROUND

Catalysts containing oxides of iron, bismuth and molybdenum, promoted with suitable elements, have long been used for conversion of propylene and/or isobutylene at elevated temperatures in the presence of ammonia and oxygen to manufacture acrylonitrile and/or methacrylonitrile. In particular, Great Britain patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with Group II elements to product acrylonitrile. In addition, U.S. Pat. Nos. 5,093,299, 5,212,137, 5,658,842 and 5,834,394 are directed to bismuth-molybdenum promoted catalysts exhibiting high yields to acrylonitrile. These catalysts may provide increased acrylonitrile production but with a corresponding decrease in yield of hydrogen cyanide and/or acetonitrile coproducts.

SUMMARY

Catalytic compositions are provided that are effective for providing increased acrylonitrile product without a significant decrease in hydrogen cyanide and/or acetonitrile production and provide an overall increase in production of acrylonitrile, hydrogen cyanide and acetonitrile.

A catalytic composition is provided that includes a complex of metal oxides having a formula:

$$Mo_{12}Bi_aFe_bA_cD_dE_eF_fG_gCe_hO_x$$

wherein A is at least one element selected from the group consisting of sodium, potassium, rubidium and cesium;

D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of a rare earth element, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury;

a is from 0.05 to 7;
b is from 0.1 to 7;
c is from 0.01 to 5;
d is from 0.1 to 12;
e is from 0 to 5;
f is from 0 to 5;
g is from 0 to 0.2;
h is from 0.01 to 5; and
x is a number of oxygen atoms required to satisfy valence requirements of other component elements. The catalytic composition includes at least about 15% m-phase plus t-phase by weight and has a weight ratio of m-phase to m-phase plus t-phase of 0.45 or greater. Amounts of m-phase and t-phase are determined using x-ray diffraction and a modified Rietveld analysis model. The catalytic composition is effective for providing an acrylonitrile yield (% AN) of 81 or greater and an acrylonitrile yield (% AN) plus acetonitrile yield (% ACN) plus hydrogen cyanide yield (% HCN) of 88 or more.

In another aspect, a process is provided for production of acrylonitrile using the catalyst compositions described herein. The process includes contacting propylene, ammonia and oxygen in a vapor phase in the presence of the metal oxide catalyst.

In another aspect, a process is provided for analyzing a metal oxide catalyst. The process includes generating x-ray diffraction data and analyzing the x-ray diffraction data using a modified Rietveld analysis. The modified Rietveld analysis model includes a $\beta$-MMoO$_4$ phase, a Fe$_2$(MoO$_4$)$_3$ phase, an m-phase and a t-phase.

BRIEF DESCRIPTION OF FIGURES

The above and other aspects, features and advantages of several aspects of the process will be more apparent from the following drawing.

FIG. 1 demonstrates a trend of increased acrylonitrile yield with increasing concentrations of m-phase with an associated fitted trend line.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

Metal oxide catalysts are provided for the production of acrylonitrile. The catalysts have a general formula and are further characterized as having at least about 15% m-phase plus t-phase by weight and a weight ratio of m-phase to m-phase plus t-phase of 0.45 or greater. In accordance with this aspect, the oxide catalyst is analyzed using X-ray diffraction (XRD). Results of the XRD analysis are then interpreted using a modified Rietveld analysis to determine amounts of m-phase and t-phase. The metal oxide catalysts provide an acrylonitrile yield (% AN) of 81 or greater and an acrylonitrile yield (% AN) plus acetonitrile yield (% ACN) plus hydrogen cyanide yield (% HCN) of 88 or more.

DEFINITIONS

Unless otherwise defined, the following terms as used throughout this specification for the present disclosure are defined as follows and can include either the singular or plural forms of definitions below defined:

As used herein "m-phase" refers to a component that is monoclinic scheelite like as determined by a modified Rietveld analysis described herein.

As used herein "t-phase" refers to a component that is tetragonal scheelite like as determined by a modified Rietveld analysis described herein.

As used herein, "acrylonitrile yield" means the percent molar yield of acrylonitrile (expressed as number without any percent sign) calculated as follows: (moles of acrylonitrile produced/moles of propylene fed to the reactor)×100.

As used herein, "acetonitrile yield" means the percent molar yield of acetonitrile (expressed as number without any percent sign) calculated as follows: (moles of acetonitrile produced/moles of propylene fed to the reactor)×100.

As used herein, "hydrogen cyanide yield" means the percent molar yield of hydrogen cyanide (expressed as number without any percent sign) calculated as follows: (moles of hydrogen cyanide produced/moles of propylene fed to the reactor)×100.

As used herein, "catalytic composition" and "catalyst" are synonymous and used interchangeably. As used herein, a "rare earth element" means at least one of lanthanum, cerium, praseodymium, neodymium, promethium, samarium, europium, gadolinium, terbium, dysprosium, holmium, erbium, thulium, ytterbium, scandium and yttrium.

Catalytic Compositions

The multi-component mixed metal oxide ammoxidation catalytic compositions include a complex of catalytic oxides represented by the following formula:

$$Mo_{12}Bi_aFe_bA_cD_dE_eF_fG_gCe_hO_x$$

wherein A is at least one element selected from the group consisting of sodium, potassium, rubidium and cesium;

D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of a rare earth element, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury;

a, b, c, d, e, f, g, h and n are, respectively, the atomic ratios of bismuth (Bi), iron (Fe), A, D, E, F, cerium (Ce) and oxygen (O), relative to 12 atoms of molybdenum (Mo), wherein a is from 0.05 to 7;
b is from 0.1 to 7;
c is from 0.01 to 5;
d is from 0.1 to 12;
e is from 0 to 5;
f is from 0 to 5;
g is from 0 to 0.2;
h is from 0.01 to 5; and
x is a number of oxygen atoms required to satisfy valence requirements of other component elements.

The catalytic composition includes at least about 15% m-phase plus t-phase by weight, in another aspect, at least about 18% m-phase plus t-phase by weight, in another aspect, at least about 20% m-phase plus t-phase by weight, and in another aspect, at least about 22% m-phase plus t-phase by weight. The composition has a weight ratio of m-phase to m-phase plus t-phase of 0.45 or greater, where amounts of m-phase and t-phase are determined using x-ray diffraction and a modified Rietveld analysis model. The catalytic composition is effective for providing an acrylonitrile yield (% AN) of at least 81% or greater, in another aspect, at least about 82% or greater, in another aspect, at least about 83% or greater, in another aspect, about 88% to about 95%, and in another aspect, about 88% to about 90%. The catalytic composition is further effective for providing an acrylonitrile yield (% AN) plus acetonitrile yield (% ACN) plus hydrogen cyanide yield (% HCN) of 88 or more, in another aspect, about 88 to about 95, and in another aspect, about 88 to about 90.

In another aspect, amounts of m-phase plus t-phase and amounts of m-phase/(m-phase+t-phase) may be as follows:

| m-phase + t-phase | m-phase/(m-phase + t-phase) |
| --- | --- |
| about 15 to about 35 | about 45 to about 70 |
| about 15 to about 25 | about 45 to about 60 |
| about 15 to about 20 | about 45 to about 55 |
| about 20 to about 35 | about 45 to about 50 |
| about 20 to about 30 | about 50 to about 55 |
| about 20 to about 25 | about 55 to about 60 |
|  | about 60 to about 65 |
|  | about 65 to about 70 |

In various aspects, the catalytic composition may include the following:

$0.15 \leq (a+b)/d \leq 1$;
$0.8 \leq h/b \leq 5$;
$0.2 \leq (a+h)/d \leq 0.6$;
$0.3 \leq (a+h)/d \leq 0.5$;
$1 \leq h/b \leq 3$; and
$1.5 \leq h/b \leq 2$.

In the aspect where $0.8 \leq h/b \leq 5$, "h/b" represents a ratio of cerium to iron in the catalytic composition which is moles of cerium (as represented by the subscript for cerium in the formula) divided by moles of iron (as represented by the subscript for cerium in the formula).

The catalyst may be supported or unsupported. Suitable supports are silica, alumina, zirconia, titania, and mixtures thereof. A support typically serves as a binder for the catalyst and results in a stronger (i.e. more attrition resistant) catalyst. However, for commercial applications, an appropriate blend of both the active phase (i.e. the complex of catalytic oxides described herein) and the support is important for obtaining an acceptable activity and hardness (attrition resistance) for the catalyst. In this aspect, the supported catalyst includes between about 30 and about 70 weight percent of the support, and in another aspect between about 40 and about 60 weight percent of the support.

In one aspect, the catalyst is supported using a silica sol. Silica sols used include less than about 600 ppm sodium, and in another aspect, less than about 200 ppm sodium. The silica sols will have an average particle diameter between about 4 nm and about 100 nm, and in another aspect, between about 15 nm and about 50 nm.

Catalyst Preparation

Catalyst compositions may be prepared using any process of catalyst preparation known in the art. Examples of catalyst preparation are described in U.S. Ser. No. 13/065,134, filed Mar. 15, 2011 and U.S. Ser. Nos. 12/661,705, 12/661,720 and 12/661,716, all filed Mar. 23, 2010, and all of which are incorporated herein by reference and summarized herein.

Elements in the catalyst composition are combined together in an aqueous catalyst precursor slurry. The aqueous catalyst precursor slurry is dried to form a catalyst precursor and the catalyst precursor is calcined to form the catalyst. In this aspect, source compounds of Bi and Ce, and optionally one or more of Na, K, Rb, Cs, Ca, a rare earth element, Pb, W, and Y are combined in an aqueous solution to form a first mixture. A source compound of molybdenum is added to the first mixture to form a precipitate slurry. The precipitate slurry is combined with source compounds of the remaining elements and of the remaining molybdenum in the catalyst to form an aqueous catalyst precursor slurry.

Modified Rietveld Analysis

Catalytic compositions may be analyzed using X-ray diffraction (XRD) and a modified Rietveld analysis. In this aspect, crystallographic phases of a catalytic composition are analyzed using XRD analysis as known in the art. A diffraction pattern of the catalytic composition is then analyzed with the modified Rietveld analysis described herein.

In accordance with the modified Rietveld analysis, a complete diffraction pattern is simulated through an ab initio calculation on the basis of the atomic structures of the individual phases from an assumed phase composition of the measuring sample. The correspondence between the simulated and measured diffraction pattern can then be effected through determination of covariance.

Rietveld analysis may be conducted using GSAS software as described in Larson et al., "General Structural Analysis System (GSAS)", Los Alamos National Laboratory Report LAUR 86-784 (2004) and in Toby, "EXPGUI, A Graphical User Interface for GSAS", J. Appl. Cryst., 34, 210-221 (2001), both of which are incorporated herein by reference. GSAS and EXPGUI are available at https://subversion.xor.aps.anl.gov/trac/EXPGUI/wiki.

The modified Rietveld model includes four phases which can be described as follows.

| Phase | Model Parameters | Refinement |
|---|---|---|
| β-MMoO$_4$ | Based on β-FeMoO$_4$ Start from literature structure: Sleight et al., Inorg. Chem. 7, 1093-8 (1968) | Unit cell and Fe occupancies |
| Fe$_2$(MoO$_4$)$_3$ | Start from literature structure: Chen, Mater. Res. Bull., 14, 1583-90 (1979) | |
| m-phase | Based on Ce$_2$(MoO$_4$)$_3$ Start from literature structure: Brixner et al., J. Solid State Chem., 5, 247-9 (1972) | Refine unit cell and Ce occupancies |
| t-phase | Based on NaBi(MoO$_4$)$_2$ Start from literature structure: Waskowska et al., Solid State Chem., 178, 2218-24 (2005) | Refine unit cell |

Starting atom coordinates are the same as reported in literature references. Starting lattice parameters are given here and differ slightly from the literature values. Thermal displacement parameters $U_{iso}$ are given in units of Å$^2$.

β-FeMoO$_4$, structure described in Sleight et al., Inorg. Chem. 7, 1093-8 (1968), which is incorporated herein by reference.
  space group C2/m, a=10.194 Å, b=9.229 Å, c=7.012Å, β=107.08°.
  $U_{iso}$ 0.01 for Fe, 0.005 for Mo, 0.02 for O.
  Starting Fe occupancies both 1.000.

Fe$_2$(MoO$_4$)$_3$, structure described in Chen, Mater. Res. Bull., 14, 1583-90 (1979), which is incorporated herein by reference.
  space group P2$_1$/a, a=15.820 Å, b=9.347 Å, c=18.196 Å, β=125.60°.
  $U_{iso}$ 0.01 for Fe and Mo, 0.02 for O.

Ce$_2$(MoO$_4$)$_3$, structure described in Brixner et al., J. Solid State Chem., 5, 247-9 (1972), which is incorporated herein by reference.
  space group C2/c, a=16.881 Å, b=11.825 Å, c=15.953 Å, β=108.73°.
  $U_{iso}$ 0.01 for Ce and Mo, 0.02 for O.
  Starting Ce occupancies all 1.000.

NaBi(MoO$_4$)$_2$, structure described in Waskowska et al., Solid State Chem., 178, 2218-24 (2005), which is incorporated herein by reference.
  space group I4$_1$/a, a=5.322 Å, c=11.851 Å.
  $U_{iso}$ 0.01 for Mo, 0.02 for Na, Bi, and O.

Background is modeled using either a 3-term cosine Fourier series or a 3-term shifted Chebyshev polynomial.

The amorphous component of the catalyst is modeled using seven Debye scattering terms with correction for thermal motion (diffuse scattering function 1 in GSAS). Each term is modeled as an Si—O vector with a thermal displacement parameter (U) of 0.05 Å$^2$. The Si—O distances of the seven terms are fixed at 1.55, 2.01, 2.53, 2.75, 3.49, 4.23, and 4.97 Å, and their amplitudes are optimized in the Rietveld fit.

The phases and parameters are introduced into the model gradually to ensure a stable refinement. At each step, 5-10 cycles of least-squares refinement are conducted to allow the model to settle down before the next components are introduced. A damping factor of 5 (i.e. 50%) on all parameters except the scale factors of the phases is used to reduce overshoots and oscillations. The procedure is as follows:

1. The starting model contains just the β-FeMoO$_4$ phase with its lattice parameters fixed and its profile Y (Lorentzian lattice strain) set to 75. Only the 3-term background function and the scale factor of the β-FeMoO$_4$ phase are varied.
2. The shift parameter (sample displacement) is added.
3. The lattice parameters of β-FeMoO$_4$ are allowed to vary.
4. The other three phases are added, all with fixed lattice parameters and profile X (Lorentzian Scherrer broadening) set to 20, and their scale factors are allowed to vary.
5. The 7 diffuse scattering terms are added and their amplitudes are allowed to vary.
6. Lattice parameters of the two scheelite-like phases are allowed to vary.
7. Profile Y of β-FeMoO$_4$ and profile X of the other three phases are allowed to vary.
8. Fe occupancies of the β-FeMoO$_4$ phase and Ce occupancies of the Ce$_2$(MoO$_4$)$_3$ phase are allowed to vary.
9. Least-squares refinement is continued until convergence, i.e. the sum of (shift/esd)$^2$ over all parameters is less than 0.01.

Ammoxidation Process

Conversions of propylene to acrylonitrile, hydrogen cyanide and acetonitrile are described in U.S. Ser. No. 13/065,134, filed Mar. 15, 2011 and U.S. Ser. Nos. 12/661,705, 12/661,720 and 12/661,716, all filed Mar. 23, 2010, which are incorporated herein by reference and summarized herein.

Catalysts provided herein are useful for conversion of propylene to acrylonitrile, hydrogen cyanide and acetonitrile by reacting in a vapor phase at an elevated temperature and pressure, the propylene with a molecular oxygen containing gas and ammonia in the presence of the catalyst.

Ammoxidation may be performed in a fluid bed reactor although other types of reactors may be utilized. An example of a fluid bed reactor that may be used is described in U.S. Pat. No. 3,230,246, which is incorporated herein by reference in its entirety. Conditions for ammoxidation are know in the art and described, for example, in U.S. Pat. Nos.

5,093,299, 4,863,891, 4,767,878 and 4,503,001, which are each incorporated herein by reference in their entirety.

Molar ratio of oxygen to olefin in the feed should range from 0.5:1 to 4:1, and in another aspect 1:1 to 3:1. The molar ratio of ammonia to propylene in the feed in the reaction may vary between 0.5:1 to 2:1. Suitable feed ratios include an ammonia to propylene molar ratio in the range of 1.0:1 to 1.3:1 and an air to propylene molar ratio of 8.0:1 to 12.0:1. The reaction may be carried out at a temperature of about 260° to about 600° C., in another aspect 310° to 500° C., and in another aspect about 350° to about 480° C. The contact time is generally not critical and may be about 0.1 to about 50 seconds, and in another aspect about 1 to about 15 seconds.

EXAMPLES

Example 1

Catalyst Preparation—
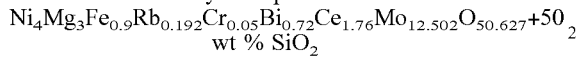

Reaction mixture A was prepared by heating 1222 ml of deionized water to 65° C. and then adding with stirring over 30 minutes ammonium heptamolybdate (1110 g) to form a clear colorless solution. Silica sol (90 ppm Na, 39 nm avg. particle size, 5461 g, 41.2 wt % silica) was then added with stirring.

Reaction mixture B was prepared by heating 241.9 ml of deionized water to 55° C. and then adding with stirring $Fe(NO_3)_3 9H_2O$ (293.9 g), $Ni(NO_3)_2 6H_2O$ (940.2 g), $Mg(NO_3)_2 6H_2O$ (621.8 g) and $Cr(NO_3)_3 9H_2O$ (16.2 g).

Reaction mixture C was prepared by heating 740.6 ml of deionized water to 65° C. and then adding with stirring over 30 minutes ammonium heptamolybdate (673 g) to form a clear colorless solution.

Reaction mixture D was prepared by (i) heating 1560 g of 50 wt % aqueous $(NH_4)_2Ce(NO_3)_6$ solution to 55° C., and (ii). while the solution was stirring and heating, sequentially adding $Bi(NO_3)_3 5H_2O$ (282.3 g) and $RbNO_3$ (22.9 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was heat treated in a rotary calciner under a ramp of 10° C./min to 450° C., holding one hour, ramping to 560° C. at 10° C./min, holding one hour and finally cooling to room temperature. The resulting calcined powder was then tested as a propylene ammoxidation catalyst.

Example 2

Catalyst Preparation—
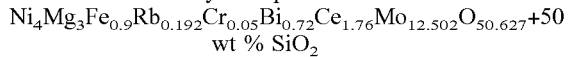

Reaction mixture A was prepared by heating 9465 ml of deionized water to 65° C. and then adding with stirring over 30 minutes ammonium heptamolybdate (8604 g) to form a clear colorless solution. Silica sol (118 ppm Na, 38.1 nm avg. particle size, 41086 g, 41.4 wt % silica) was then added with stirring.

Reaction mixture B was prepared by heating 1828.9 ml of deionized water to 55° C. and then adding with stirring $Fe(NO_3)_3 9H_2O$ (2221.9 g), $Ni(NO_3)_2 6H_2O$ (7107.9 g), $Mg(NO_3)_2 6H_2O$ (4700.5 g) and $Cr(NO_3)_3 9H_2O$ (122.3 g).

Reaction mixture C was prepared by heating 2686.3 ml of deionized water to 65° C. and then adding with stirring over 30 minutes ammonium heptamolybdate (2442 g) to form a clear colorless solution.

Reaction mixture C' was prepared by heating 2686.3 ml of deionized water to 65° C. and then adding with stirring over 30 minutes ammonium heptamolybdate (2442 g) to form a clear colorless solution.

Reaction mixture D was prepared by (i) heating 5896 g of 50 wt % aqueous $(NH_4)_2Ce(NO_3)_6$ solution to 55° C., and (ii). while the solution was stirring and heating, sequentially adding $Bi(NO_3)_3 5H_2O$ (1067.1 g) and $RbNO_3$ (86.5 g) resulting in a clear orange solution.

Reaction mixture D' was prepared by (i) heating 5896 g of 50 wt % aqueous $(NH_4)_2Ce(NO_3)_6$ solution to 55° C., and (ii). while the solution was stirring and heating, sequentially adding $Bi(NO_3)_3 5H_2O$ (1067.1 g) and $RbNO_3$ (86.5 g) resulting in a clear orange solution.

Reaction mixture E was prepared by adding with stirring reaction mixture B to reaction mixture A.

Reaction mixture F was prepared by adding reaction mixture C to reaction mixture D. Reaction mixture F' was prepared by adding reaction mixture C' to reaction mixture D'. In each case this resulted in precipitation of an orange solid. The resulting mixture was the precipitate slurry. Stirring of Reaction mixtures F and F' was continued for 15 minutes while the temperature was maintained in the 50-55° C. range.

Reaction mixture F, followed by reaction mixture F' were then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried at an inlet/outlet temperature of 325/140° C. The resulting powder was denitrified in a rotary calciner at 850° F. for 50 min followed by calcining in a rotary calciner to 1050° F. for 110 minutes. The resulting calcined powder was then tested as a propylene ammoxidation catalyst.

Comparative Example 1

Catalyst Preparation—
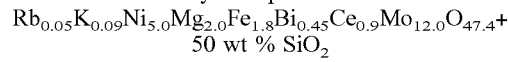

A 17.9 wt % $HNO_3$ solution was made by diluting 64 ml concentrated $HNO_3$ to 250.0 ml with deionized water. A 30 wt % silica sol mixture was prepared by adding 208.3 g deionized water to 625 g 40 wt % $SiO_2$ sol (22 nm avg particle size).

A solution of metal nitrates was prepared by dissolving 70.38 $Fe(NO_3)_3.9H_2O$, 140.73 g $Ni(NO_3)_2.6H_2O$, 49.63 g $Mg(NO_3)_2.6H_2O$, 37.82 g $Ce(NO_3)_3.6H_2O$, 21.13 g $Bi(NO_3)_3.5H_2O$, 0.881 g $KNO_3$, and 0.714 g $RbNO_3$ in 188.85 g of a 17.9 wt % aqueous nitric acid solution, and heated to 55° C. This metal nitrate solution was added to 833.3 g of the 30 wt % $SiO_2$ sol. To this resulting mixture, a 65° C. solution of 205.04 g of [(NH$_4$)$_2$Mo$_7$O$_{24}$.4H$_2$O] in 425 g deionized water was added to form a light green slurry. The slurry was stirred for one hour while cooling to 40° C. The slurry was then transferred to a polyethylene container, agitated for 16 hours at room temperature, and spray dried at an inlet/outlet temperature of 325/140° C.

The spray dried catalyst precursor obtained was calcined for one hour in a 400° C. oven and then for two hours in a 590° C. oven. The resulting calcined powder was then tested as a propylene ammoxidation catalyst.

Results of catalyst testing form all of the Examples was as follows:

| Example No. | wt % m-phase/ (m-phase + t-phase) | wt % (m-phase + t-phase) | % ACN yield | % ACN + HCN + ACN yields |
|---|---|---|---|---|
| Example 1 | 53.7 | 24.2 | 84.0 | 89.8 |
| Example 2 | 49.4 | 24.6 | 82.8 | 88.9 |
| Comparative Example 1 | 55.5 | 4.4 | 78.3 | 86.0 |

FIG. 1 demonstrates further a trend of increased acrylonitrile yield with increasing concentrations of m-phase (expressed as % monoclinic scheelite phase, expressed as weight fraction) in the catalyst. The scatter in the data is to be expected due to normal experimental error and differences in the catalyst preparation protocol including batch size, drying and calcination protocols, some variation in catalyst formulation, and experimental error in the quantitative determination of the phase composition of the catalyst. The fitted trend line again indicates an increase in acrylonitrile yield as the m-phase (expressed as % monoclinic scheelite) content of the catalyst increases.

Example 3

X-Ray Diffraction Analysis

Catalyst samples were analyzed as received with no grinding. Two pieces of double-sided tape were placed side-by-side on a quartz surface of a zero-background cell and the catalyst was sprinkled on the tape to cover it completely. The cell was tapped gently to remove excess catalyst. The edges of the cell may be cleaned using a paint brush. Typical conditions for a Bruker D8 Advance diffractometer were as follows:
sample spinning
Cu Kα radiation
X-ray generator 40 KV, 40 mA
divergence slit 0.3°
antiscattering slit 0.5°
Vantec detector discriminator lower level 0.1V, window width 0.5V
scan range 5°-100° 2θ
step size 0.00729689°
time/step 1 sec
total scan time 3:46

While the invention herein disclosed has been described by means of specific embodiments, examples and applications thereof, numerous modifications and variations could be made thereto by those skilled in the art without departing from the scope of the invention set forth in the claims.

What is claimed is:

1. A process for production of acrylonitrile comprising contacting propylene, ammonia and oxygen in a vapor phase in the presence of a metal oxide catalyst, the metal oxide catalyst having a formula:

$$Mo_{12}Bi_aFe_bA_cD_dE_eF_fG_gCe_hO_x$$

wherein A is at least one element selected from the group consisting of sodium, potassium, rubidium and cesium;
D is at least one element selected from the group consisting of nickel, cobalt, manganese, zinc, magnesium, calcium, strontium, cadmium and barium;
E is at least one element selected from the group consisting of chromium, tungsten, boron, aluminum, gallium, indium, phosphorus, arsenic, antimony, vanadium and tellurium;
F is at least one element selected from the group consisting of a rare earth element, titanium, zirconium, hafnium, niobium, tantalum, aluminum, gallium, indium, thallium, silicon, germanium, and lead;
G is at least one element selected from the group consisting of silver, gold, ruthenium, rhodium, palladium, osmium, iridium, platinum and mercury;
a is from 0.05 to 7;
b is from 0.1 to 7;
c is from 0.01 to 5;
d is from 0.1 to 12;
e is from 0 to 5;
f is from 0 to 5;
g is from 0 to 0.2;
h is from 0.01 to 5; and
x is a number of oxygen atoms required to satisfy valence requirements of other component elements,
wherein the catalytic composition includes at least about 15% m-phase plus t-phase by weight and has a weight ratio of m-phase to m-phase plus t-phase of 0.45 or greater, where amounts of m-phase and t-phase are determined using x-ray diffraction and a modified Rietveld analysis model,
wherein the catalytic composition is effective for providing an acrylonitrile yield (% AN) of 81 or greater and an acrylonitrile yield (% AN) plus acetonitrile yield (% ACN) plus hydrogen cyanide (% HCN) of 88 or more.

2. The process of claim 1 wherein the modified Rietveld analysis model includes four major phases.

3. The process of claim 1 wherein the catalyst composition includes a support selected from the group consisting of silica, alumina, zirconia, titania, or mixtures thereof.

4. The process of claim 1 wherein the catalytic composition includes at least about 18% m-phase plus t-phase by weight.

5. The process of claim 4 wherein the catalytic composition includes at least about 20% m-phase plus t-phase by weight.

6. The process of claim 5 wherein the catalytic composition includes at least about 22% m-phase plus t-phase by weight.

7. The process of claim 1 wherein the acrylonitrile yield (% AN) is 82 or greater.

8. The process of claim 7 wherein the acrylonitrile yield (% AN) is 83 or greater.

* * * * *